(12) United States Patent
Jeffrey et al.

(10) Patent No.: US 6,695,776 B1
(45) Date of Patent: Feb. 24, 2004

(54) EQUINE DENTAL SPECULUM

(75) Inventors: Louis Dale Jeffrey, Glenns Ferry, ID (US); Wiliam Lloyd Jeffrey, Glenns Ferry, ID (US)

(73) Assignee: World Wide Equine, Inc., Glenns Ferry, ID (US)

( * ) Notice: Subject to any disclaimer, the term of this patent is extended or adjusted under 35 U.S.C. 154(b) by 0 days.

(21) Appl. No.: 10/334,585

(22) Filed: Dec. 31, 2002

(51) Int. Cl.⁷ ............................... A61B 1/32; A61C 5/00
(52) U.S. Cl. ......................................... 600/243; 433/140
(58) Field of Search .................................. 600/184, 201, 600/235, 237, 243, 244; 433/1, 140

(56) References Cited

U.S. PATENT DOCUMENTS

| | | |
|---|---|---|
| 120,062 A | 10/1871 | Hallock |
| 314,527 A | 3/1885 | Green |
| 402,068 A | 4/1889 | Vrannell |
| 457,911 A | 8/1891 | Edwards |
| 477,838 A | 6/1892 | Elliott |
| 893,589 A | 7/1908 | Jenkins |
| 1,137,585 A * | 4/1915 | Craig, Jr. |
| 1,331,542 A | 2/1920 | Vose |
| 1,694,713 A | 12/1928 | Maclean, Jr. |
| 2,011,445 A | 8/1935 | Hiner |
| 2,096,083 A | 10/1937 | Berzina |
| 5,704,901 A | 1/1998 | Meister |
| 5,718,665 A | 2/1998 | Stubbs |
| 6,234,962 B1 | 5/2001 | Williams |

* cited by examiner

*Primary Examiner*—Eduardo C. Robert
*Assistant Examiner*—Anuradha Ramana
(74) *Attorney, Agent, or Firm*—Stephen M. Nipper; Frank J. Dykas; Robert L. Shaver

(57) ABSTRACT

An equine dental speculum maintenance system utilizing rotatable and replaceable wear components in order to extend the useful life of an equine dental speculum. Both the toothed rack and the pawl are rotatable and replaceable.

4 Claims, 3 Drawing Sheets

EQUINE DENTAL SPECULUM

BACKGROUND OF THE INVENTION

Field of the Invention

The present invention generally relates to veterinary dental speculums, and more particularly relates to methods and apparatuses for the maintenance and repair of veterinary mouth speculums, as well as improved veterinary mouth speculums, namely equine dental speculums.

Background Information

A veterinary dental speculum is utilized to hold the mouth of an animal, such as a horse, open while dental and/or medical attention is given to the animal. Obviously, when one has his/her hand within an animal's mouth, it is best if some means of restraining that animal from biting down is provided.

Various different types of veterinary dental speculums are shown in the prior art. For instance, Hallock (U.S. Pat. No. 120,062) discloses an improved animal gag utilizing a ring that is placed in the animal's mouth. The Green patent (U.S. Pat. No. 314,527) discloses a device for opening an animal's mouth utilizing a pair of handles used to force the animal's mouth open with a set screw able to be tightened, thereby holding the animal's mouth open. The Crannell patent (U.S. Pat. No. 402,068) discloses a drenching bit utilized to hold open the mouth of a horse. The Crannell drenching bit utilizes a ratcheting device to ratchet the horse's mouth open. The Edwards veterinary mouth opener (U.S. Pat. No. 457,911) discloses another device utilizing a ratcheting means.

The Vose patent (U.S. Pat. No. 1,331,542) discloses a dental halter and mouth speculum utilized to force the mouth of the animal open and hold it in an open state. The Vose device utilizes a bar with teeth that is forced into a locking engagement with retaining stirrups that hold the animal's mouth open. The MacLean, Jr. patent (U.S. Pat. No. 1,694,713) discloses animal mouth tongs utilizing a ratcheting mechanism for holding an animal's mouth open. The Hiner patent (U.S. Pat. No. 2,011,445) discloses a speculum having a pair of top and bottom jaw isolators that can be forced apart. The Hiner speculum utilizes a nose strap as well as a neck strap to strap the device onto the animal's head.

The Berzina patent (U.S. Pat. No. 2,096,083) discloses a veterinary mouth speculum utilizing a pair of jaw isolators that can be separated through use of a ratcheting means. The Meister patent (U.S. Pat. No. 5,704,901) discloses an equine speculum utilizing a pair of jaw isolators using a ratcheting means located below the front of the jaw of the animal to separate the jaw isolators from one another, thereby holding the animal's mouth open. The Stubbs patent (U.S. Pat. No. 5,718,665) discloses a speculum that is forced into the animals mouth, held on through the use of a neck strap, which forces the animal's mouth apart through the tightening of a threaded rod screw jack. Finally, the Williams patent (U.S. Pat. No. 6,234,962) discloses an equine dental speculum, which is forced into the mouth of the horse and which holds the horse's mouth open.

One of the major problems in the prior art devices is the fact that through repeated use, components fail and wear thereby causing a safety risk to the operator as well as to the animal on which the device is used. What is needed is a method and apparatus for maintaining a dental speculum in working order thereby both extending the life of the dental speculum as well as increasing the safety of its use. What is also needed is an improved speculum. Embodiments of the present invention solve these needs.

Additional objects, advantages and novel features of the invention will be set forth in part in the description which follows and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

The present invention is an improved veterinary speculum. One embodiment of the present invention comprises an improved equine dental speculum system. This system comprising the steps. The first step is providing an equine dental speculum having at least one ratcheting mechanism. This ratcheting mechanism comprising a rack of teeth upon which a pawl is configured to be moved along. This speculum comprising an upper frame and a lower frame. The ratcheting mechanism utilized to move an upper frame front end apart from a lower frame front end. The second step is providing a rack of teeth that is configured to be removed from the ratcheting mechanism, rotated and reinstalled within the ratcheting mechanism. This functionality thereby providing for uniformity in wear of the rack of teeth. The third step is providing a pawl that is configured to be removed from the ratcheting mechanism, rotated, and reinstalled within the ratcheting mechanism. This functionality thereby providing for uniformity in wear of the pawl.

A second embodiment of the present invention is a system of increasing the useable life span of an equine dental speculum. This system comprising a number of steps. First, providing a speculum having an upper frame pivotally attached to a lower frame at pivot for connecting an upper frame distal end to a lower frame distal end. This upper frame having a proximal end opposite the upper frame distal end. The lower frame having a proximal end opposite the lower frame distal end. The speculum further comprising a ratcheting mechanism for opening the mouth of a horse by moving the upper frame distal end away from the lower frame distal end. Wherein the lower frame defines a rack connection slot for receiving therein a toothed rack able to cooperate with a pawl of a ratcheting mechanism to move the upper frame distal end away from the lower frame distal end. The rack connection slot having a first end extending to a second end. Second, providing a toothed rack having a first end extending to a second end. The rack is configured for attachment to the track connection slot so that the rack first end is adjacent the slot first end and the rack second end is adjacent the slot second end. The rack is also configured for attachment to the rack connection slot so that the rack first end is adjacent the slot second end and the rack second end is adjacent the slot first end.

In this embodiment, it is likewise preferred that the ratcheting mechanism comprises a pawl connection slot for receiving the pawl therein. This pawl connection slot having a first end extending to a second end, with the pawl having a first end extending to a second end. The pawl being configured for attachment to the pawl connection slot so that the pawl first end is adjacent the pawl connection slot first end and the pawl second end is adjacent the pawl connection slot second end. The pawl preferably also configured for attachment to the pawl connection slot so that the pawl first end is adjacent the pawl connection slot second end and the pawl second end is adjacent the pawl connection slot first end.

In a fourth embodiment, the present invention comprises an equine dental speculum for utilization on the mouth of a horse. This speculum comprising an upper frame assembly, a lower frame assembly, a pair of ratchet assemblies, a neck strap, and a nose strap. The upper frame assembly for supporting the upper teeth of the horse. The upper frame assembly comprising a first upper jaw piece for extending along a first side of the horse's mouth, a generally crescent-shaped upper mouth piece for receiving the upper teeth and lip of the horse, and a second upper jaw piece for extending along the second side of said horse's mouth. These upper jaw pieces having proximal ends and distal ends, wherein the proximal ends connect to the mouth piece. The upper frame assembly having a nose strap slot generally midway along each of the jaw piece to receive the nose strap. The upper frame assembly having a head strap slot adjacent the distal end of each of the jaw pieces for receiving the head strap.

The lower frame assembly for supporting the lower teeth of the horse. This lower frame assembly comprising a first lower jaw piece for extending along a first side of the horse's mouth, a generally crescent-shaped lower mouth piece for receiving the lower teeth and lip of said horse, and a second lower jaw piece for extending along the second side of the horse's mouth. The lower jaw pieces having proximal ends and distal ends. The proximal ends connecting to the mouth piece. The distal ends configured to join corresponding upper jaw piece distal ends at first and second pivot joints. A rack connection slot is defined in each of the lower jaw pieces. These rack connections each configured to receive therein a rack. These racks each having an upper surface comprising a plurality of teeth.

The ratchet assemblies are for elevating the upper frame from the lower frame, with one of the ratchet assemblies utilized on each lower jaw piece. Each ratchet assembly comprising a frame having a handle for digital manipulation. This frame having a pawl for interfitting cooperation with a portion of the teeth of the rack. The pawl held in engagement with the teeth through use of a ratchet assembly spring. The handle can be manipulated to move the pawl along the teeth. Each ratchet assembly further comprising a ratchet connection for connecting the ratchet with a link. This link interconnecting the ratchet to the corresponding upper jaw piece, whereby actuation of the handle results in pushing the link, which moves the upper frame front end away from the lower frame front end. A nose strap for attaching said speculum to the nose of said horse and a neck strap for attaching said speculum to the neck of said horse are also preferably provided.

Still other objects and advantages of the present invention will become readily apparent to those skilled in this art from the following detailed description wherein I have shown and described only the preferred embodiment of the invention, simply by way of illustration of the best mode contemplated by carrying out my invention. As will be realized, the invention is capable of modification in various obvious respects all without departing from the invention. Accordingly, the drawings and description of the preferred embodiment are to be regarded as illustrative in nature, and not as restrictive in nature.

DESCRIPTION OF THE PREFERRED EMBODIMENTS

Figure 1:
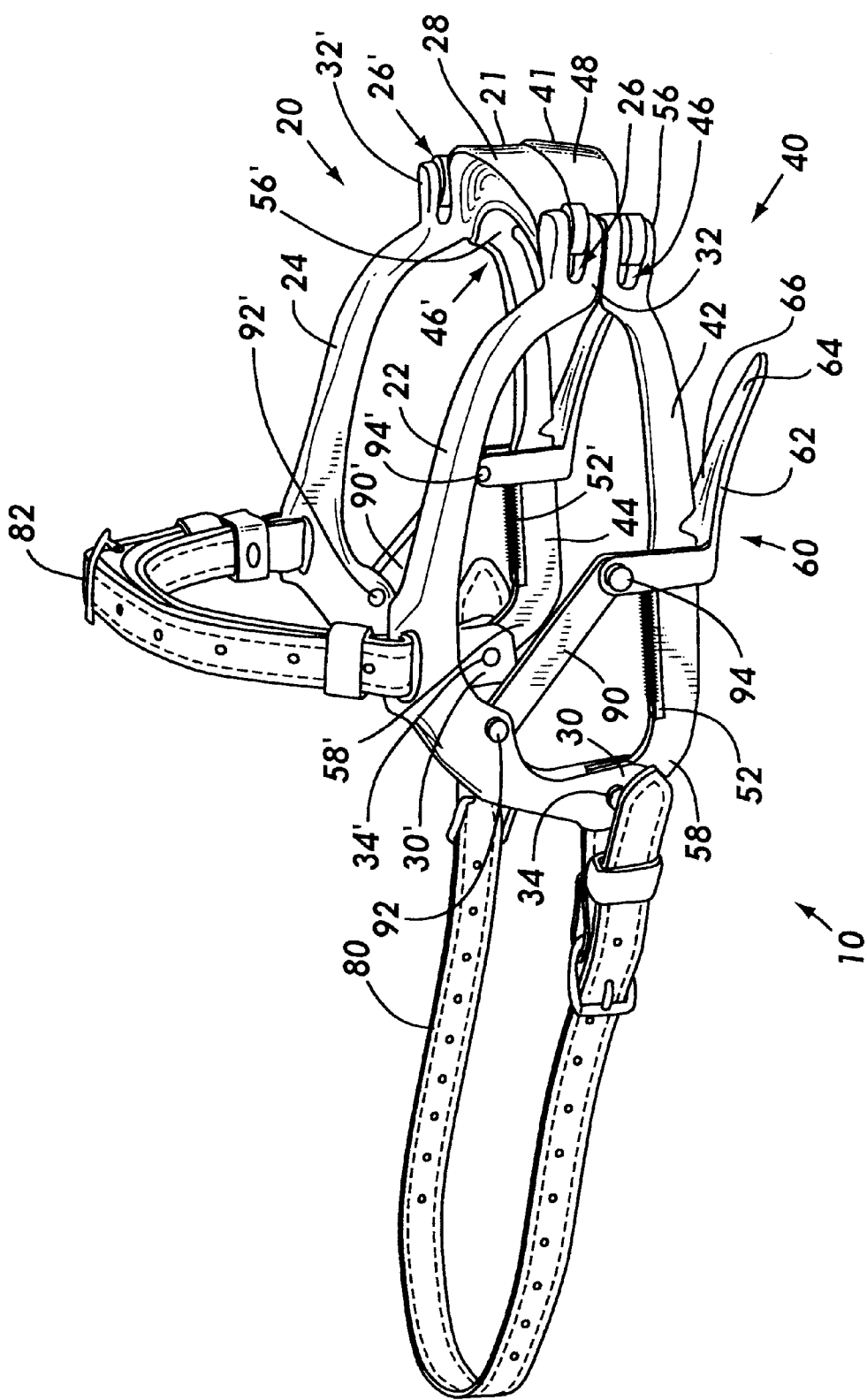
FIG. 1 is a perspective view of one embodiment of the present invention.

While the invention is susceptible of various modifications and alternative constructions, certain illustrated embodiments thereof have been shown in the drawings and will be described below in detail. It should be understood, however, that there is no intention to limit the invention to the specific form disclosed, but, on the contrary, the invention is to cover all modifications, alternative constructions, and equivalents falling within the spirit and scope of the invention as defined in the claims.

The present invention is an improved veterinary speculum, particularly an improved equine dental speculum and the parts thereof.

Referring initially to FIG. 1, shown is a preferred embodiment of the present invention. In this figure, the improved speculum 10 is shown in perspective view. This improved speculum 10 having an upper frame 20 and a lower frame 40. Both the upper and lower frames being generally "U" in shape and pivotally joined together at a pair of pivot joints 34, 34'. This pivot being made at the distal ends (30, 30', 58, 58') of the upper frame and the lower frame.

The upper frame 20 comprises a first upper jaw piece 22 and a second upper jaw piece 24. The distal ends 30, 30' of these upper jaw pieces connect with the lower frame at the pivot joints 34, 34'. The proximal ends 32, 32' of the first upper jaw piece 22 and the second upperjaw piece 24 connect at clevis joints 26, 26' to an upper mouthpiece 28. This upper mouthpiece for contacting the upper mouth portion of the animal upon which the speculum is utilized.

It is preferred that a nose strap 82 connect between the first upper jaw piece and second upper jaw piece for resting across the bridge of the nose of the animal upon which the speculum is utilized. It is preferred that this nose strap be adjustable. It is further preferred that a neck strap 80 attach to the distal ends 30, 30' of the first and second upper jaw pieces. This neck strap extending across the back of the neck of the animal thereby securely holding the speculum on the animal's head. The orientation, location, and utilization of these neck and nose straps being preferred optional and potentially configured otherwise, including being absent.

Figure 3:
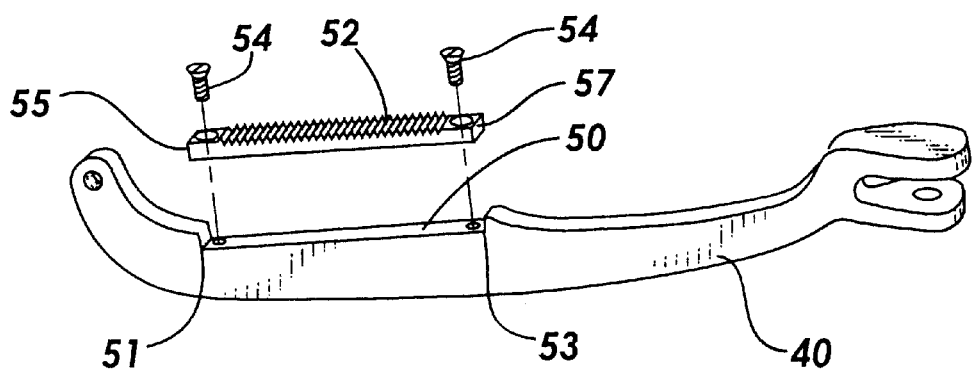
FIG. 3 shows one embodiment of an interchangeable ratchet teeth plate utilized with the embodiment of the present invention.

The lower frame 40 comprises a first lower jaw piece 42 and a second lower jaw piece 44. These lower jaw pieces connecting with a lower mouthpiece 48 via a pair of clevis joints 46, 46'. The distal ends 58, 58' of these lowerjaw pieces connecting at the pivot joints 34, 34' with the jaw pieces of the upper frame. Located within each of the lower jaw pieces is a notch formed therein, particularly as shown in FIG. 3. This notch or "rack connection" 50 allowing an interchangeable, rotatable, and replaceable rack 52, 52' to be placed therein. This rack connection having a first end 51 extending to a second end 53. The rack 52 having a first end 55 extending to a second end 57. It is preferred that the rack be oriented within the rack connection so that the first end of the rack be located adjacent the first end of the rack connection and the second end of the rack be located adjacent the second end of the rack. As the present invention is normally used, the teeth on the rack will eventually wear. When this wear occurs, the rack can be removed, rotated 180 degrees, and reinserted into the rack connection so that the rack first end is adjacent the rack connection second end and the rack second end is adjacent the rack connection first end.

In the preferred embodiment, a pair of screws 54 are utilized to secure the rack 52 to the rack connection 50. Other means of securing the rack to the rack connection may be utilized, including, but are not limited to, adhesives, dove tails, other friction fits, screws, bolts, pins, and other means of attachment.

Figure 2:
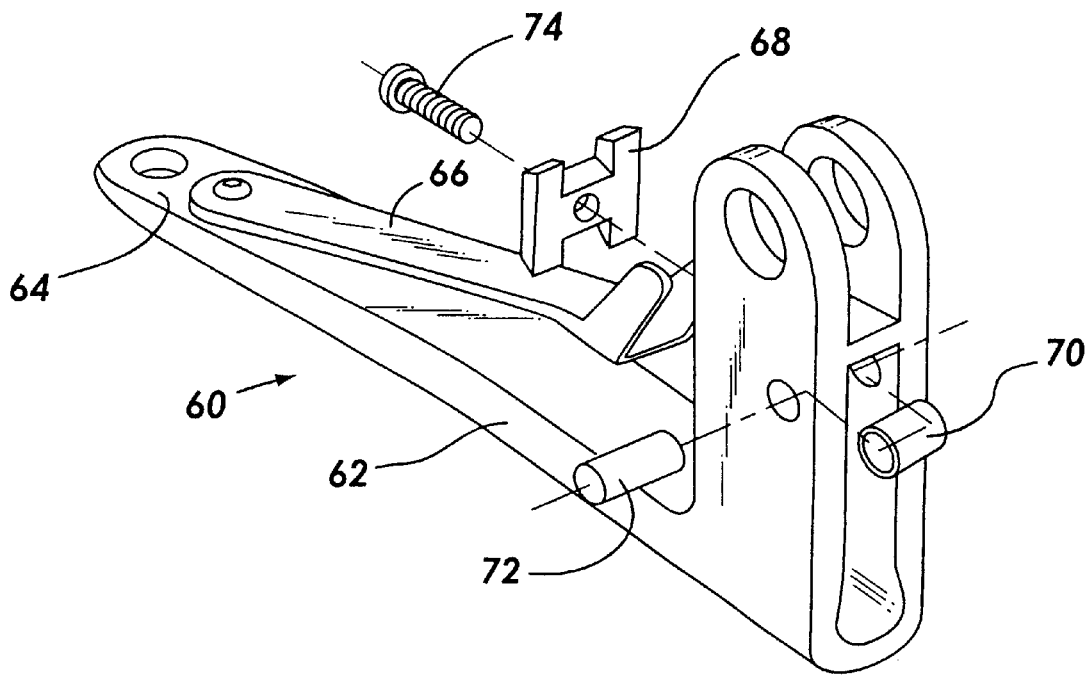
FIG. 2 shows an exploded, perspective view of one embodiment of a ratchet handle utilizing the present invention.
Figure 4:
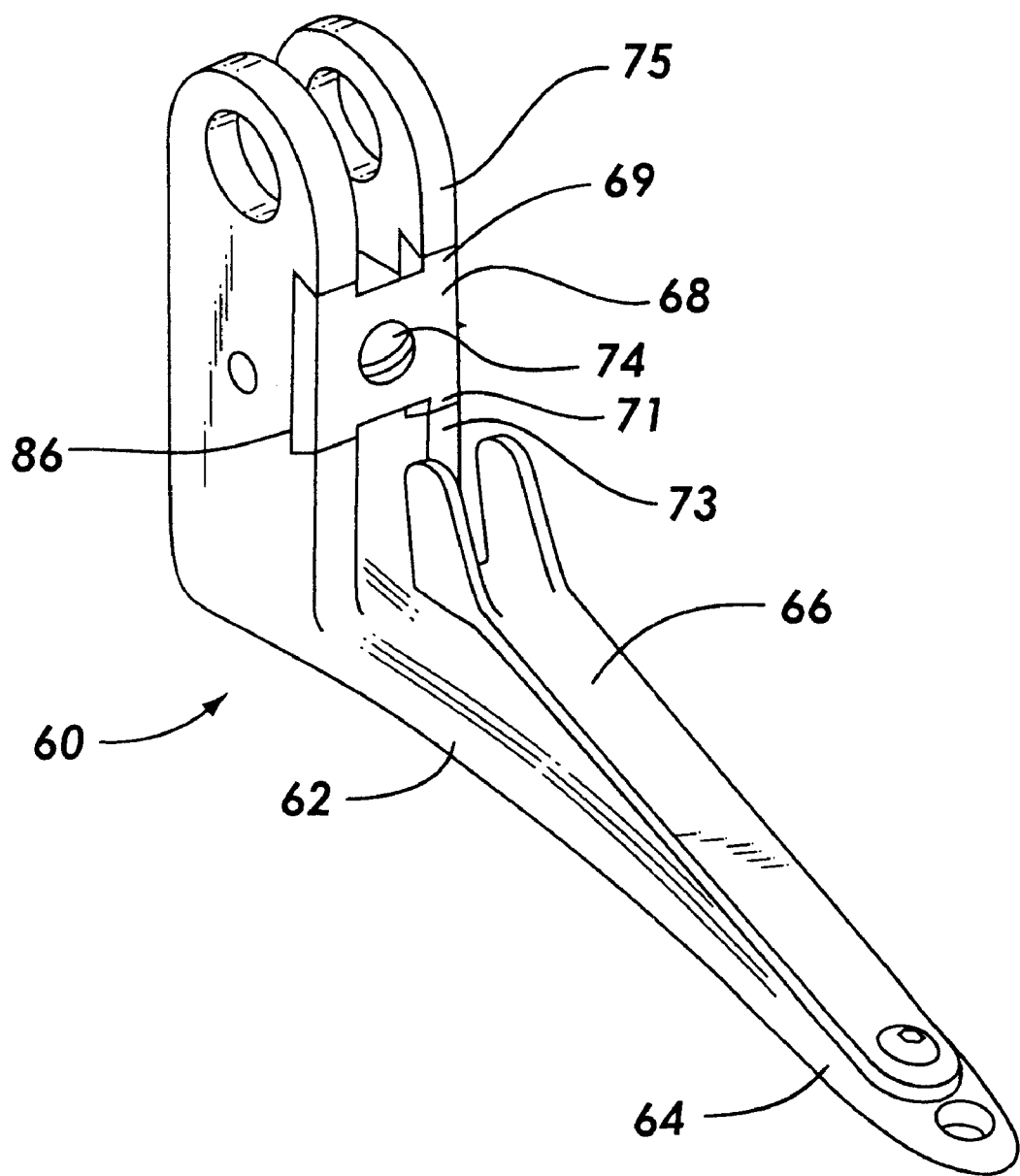
FIG. 4 shows an opposite end perspective view, non-exploded, of the embodiment of FIG. 2.

Referring now to FIGS. 2 and 4, the rack 52 is configured for cooperation with a dog or "pawl" 68 of the lower release lever or ratchet assembly 60. This ratchet assembly 60 has a ratchet frame 62 further comprising a handle 64 and a spring 66. This spring 66 configured to hold the pawl 68 in engagement with the rack 52, as shown in FIG. 1. A roller 70 is preferably held within the ratchet frame 62 via a pin 72 to provide for easier movement of the ratchet assembly along the rack.

In the preferred embodiment, the pawl 68 is removably and rotatably interchangeable through use of a screw 74. In this way, when one surface of the pawl wears, the user is able to remove the pawl via removing said screw 74, rotate the pawl (preferably 180 degrees), and replace the pawl back within the pawl connection 76. The ratchet frame 62 having a pawl holder first end 75 and a pawl holder second end 73. The pawl 68 having a first end 69 and a second end 71. Thus, in the preferred embodiment, initially, the pawl first end 69 will engage the pawl holder first end 75 and the pawl second end 71 will engage the pawl holder second end 73. The pawl can be rotated so that the pawl first end 69 will engage the pawl holder second end 73 and the pawl second end 71 will engage the pawl holder first end 75. Additionally, the pawl may be configured with four sides able to engage the teeth rather than the two shown.

Thus, as the present invention is used, the wearable components (the pawl and the rack) are configured to be removed as necessary, rotated, and/or replaced, thereby providing for an extended life of the speculum. Also, when wear becomes sufficient, complete replacement of the dog and the rack can be done without needing to replace the entire speculum. The speculum itself, including a majority of the components, is comprised of tool grade stainless steel. Thus, the rotatability, interchangeability, and replaceability of the rack and dog greatly reduce the maintenance and ownership costs because the entire unit need not be replaced, but only the parts that wear.

It is preferred that at least one link 90 (90') connect between the ratchet 60 at a ratchet connection 94 (94') and an upper frame connection 92 (92'). This link 90 (90') serving as the means for separating the upper frame from the lower frame in a locked position. As the ratchet assembly with pawl is advanced along the rack, the ratchet assembly draws nearer the distal ends of the lower jaw piece, pushing the link upwards, thereby pushing the proximal ends of the upper and lower jaw pieces apart. This action forces and holds the mouth of the animal open.

While there is shown and described the present preferred embodiment of the invention, it is to be distinctly understood that this invention is not limited thereto but may be variously embodied to practice within the scope of the following claims. From the foregoing description, it will be apparent that various changes may be made without departing from the spirit and scope of the invention as defined by the following claims.

We claim:

1. An equine dental speculum, said speculum comprising:
    at least one ratcheting mechanism, said ratcheting mechanism comprising a rack of teeth upon which a pawl is able to be moved along, said speculum comprising an upper frame and a lower frame, said ratcheting mechanism utilized to move an upper frame front end apart from a lower frame front end;
    a rack of teeth, said rack of teeth configured to be removed from said ratcheting mechanism, rotated and reinstalled within said ratcheting mechanism thereby providing for uniformity in wear of said rack of teeth; and
    a pawl, said pawl configured to be removed from said ratcheting mechanism, rotated and reinstalled within said ratcheting mechanism, thereby providing for uniformity in wear of said pawl.

2. An equine dental speculum, said speculum comprising:
    an upper frame pivotally attached to a lower frame at a pivot connecting an upper frame distal end to a lower frame distal end, said upper frame having a proximal end opposite said upper frame distal end, said lower frame having a proximal end opposite said lower frame distal end, said speculum further comprising a ratcheting mechanism for opening the mouth of a horse by moving said upper frame distal end away from said lower frame distal end, wherein said lower frame defines a rack connection slot for receiving therein a toothed rack able to cooperate with a pawl of a ratcheting mechanism to move said upper frame distal end away from said lower frame distal end, said rack connection slot having a first end extending to a second end; and
    a toothed rack having a first end extending to a second end, wherein said rack is configured for attachment to said rack connection slot so that said rack first end is adjacent said slot first end and said rack second end is adjacent said slot second end, wherein said rack is also configured for attachment to said rack connection slot so that said rack first end is adjacent said slot second end and said rack second end is adjacent said slot first end.

3. The speculum of claim 2, wherein said ratcheting mechanism comprises a pawl connection slot for receiving said pawl therein, said pawl connection slot having a first end extending to a second end, said pawl having a first end extending to a second end, wherein said pawl is configured for attachment to said pawl connection slot so that said pawl first end is adjacent said pawl connection slot first end and said pawl second end is adjacent said pawl connection slot second end, wherein said pawl is also configured for attachment to said pawl connection slot so that said pawl first end is adjacent said pawl connection slot second end and said pawl second end is adjacent said pawl connection slot first end.

4. An equine dental speculum for utilization on the mouth of a horse, said speculum comprising:
    an upper frame assembly for supporting the upper teeth of said horse, said upper frame assembly comprising a first upper jaw piece for extending along a first side of said horse's mouth, a generally crescent-shaped upper mouth piece for receiving the upper teeth and lip of said horse, and a second upper jaw piece for extending along said second side of said horse's mouth, said upper jaw pieces having proximal ends and distal ends, wherein said proximal ends connect to said mouth piece, said upper frame assembly having a nose strap slot generally midway along each of said jaw piece to receive a nose strap, said upper frame assembly having a head strap slot adjacent said distal end of each of jaw pieces for receiving a head strap;

a lower frame assembly for supporting the lower teeth of said horse, said lower frame assembly comprising a first lowerjaw piece for extending along a first side of said horse's mouth, a generally crescent-shaped lower mouth piece for receiving the lower teeth and lip of said horse, and a second lowerjaw piece for extending along said second side of said horse's mouth, said lower jaw pieces having proximal ends and distal ends, wherein said proximal ends connect to said mouth piece, wherein said distal ends join corresponding upper jaw piece distal ends at first and second pivotjoints, a rack connection slot defined in each of said lowerjaw pieces, each of said rack connections configured to receive therein a rack, said racks each having an upper surface comprising a plurality of teeth;

a pair of ratchet assemblies for elevating said upper frame from said lower frame, one of said ratchet assemblies utilized on each lowerjaw piece, each ratchet assembly comprising a frame having a handle for digital manipulation, said frame having a pawl for interfitting cooperation with said teeth of said rack, said pawl held in engagement with said teeth through use of a ratchet assembly spring, wherein said handle can be manipulated to move said pawl along said teeth, each ratchet assembly further comprising a ratchet connection for connecting said ratchet with a link, said link interconnecting said ratchet to said corresponding upper jaw piece, whereby actuation of said handle results in pushing said link thereby moving said upper mouth piece away from said lower mouth piece;

a nose strap for attaching said speculum to the nose of said horse; and a neck strap for attaching said speculum to the neck of said horse.

\* \* \* \* \*